US012697100B2

(12) United States Patent
Nishigaki

(10) Patent No.: US 12,697,100 B2
(45) Date of Patent: Aug. 4, 2026

(54) ULTRASOUND DIAGNOSTIC APPARATUS, ULTRASOUND DIAGNOSTIC SYSTEM, ULTRASOUND IMAGE GENERATION METHOD, AND STORAGE MEDIUM

(71) Applicant: Konica Minolta, Inc., Tokyo (JP)

(72) Inventor: Morio Nishigaki, Fujisawa (JP)

(73) Assignee: KONICA MINOLTA, INC., Tokyo (JP)

(*) Notice: Subject to any disclaimer, the term of this patent is extended or adjusted under 35 U.S.C. 154(b) by 74 days.

(21) Appl. No.: 18/958,059

(22) Filed: Nov. 25, 2024

(65) Prior Publication Data

US 2025/0169798 A1 May 29, 2025

(30) Foreign Application Priority Data

Nov. 28, 2023 (JP) ................................. 2023-200488

(51) Int. Cl.
*A61B 8/00* (2006.01)
(52) U.S. Cl.
CPC ................................. *A61B 8/5223* (2013.01)
(58) Field of Classification Search
CPC ................................................... A61B 8/5223
See application file for complete search history.

(56) References Cited

U.S. PATENT DOCUMENTS

| | | | | |
|---|---|---|---|---|
| 6,628,983 | B1* | 9/2003 | Gagnon | G01T 1/1648 |
| | | | | 600/431 |
| 2003/0236459 | A1* | 12/2003 | Loftman | G01S 7/52026 |
| | | | | 600/437 |
| 2005/0101867 | A1* | 5/2005 | Johnson | G01S 15/8915 |
| | | | | 600/459 |
| 2018/0341857 | A1* | 11/2018 | Lee | G06N 3/082 |
| 2019/0246927 | A1* | 8/2019 | Väyrynen | A61B 5/374 |
| 2020/0286369 | A1* | 9/2020 | Ferrin | G06V 20/56 |
| 2021/0059796 | A1* | 3/2021 | Weiss | G06T 7/12 |
| 2021/0183063 | A1* | 6/2021 | Thomson | G16H 20/30 |

FOREIGN PATENT DOCUMENTS

| | | |
|---|---|---|
| JP | 3665408 B2 | 6/2005 |
| JP | 2021115212 A | 8/2021 |

* cited by examiner

*Primary Examiner* — Bo Joseph Peng
(74) *Attorney, Agent, or Firm* — CANTOR COLBURN LLP

(57) ABSTRACT

An ultrasound diagnostic apparatus includes a first hardware processor. The first hardware processor is configured to estimate and generate weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

6 Claims, 10 Drawing Sheets

FIG.6

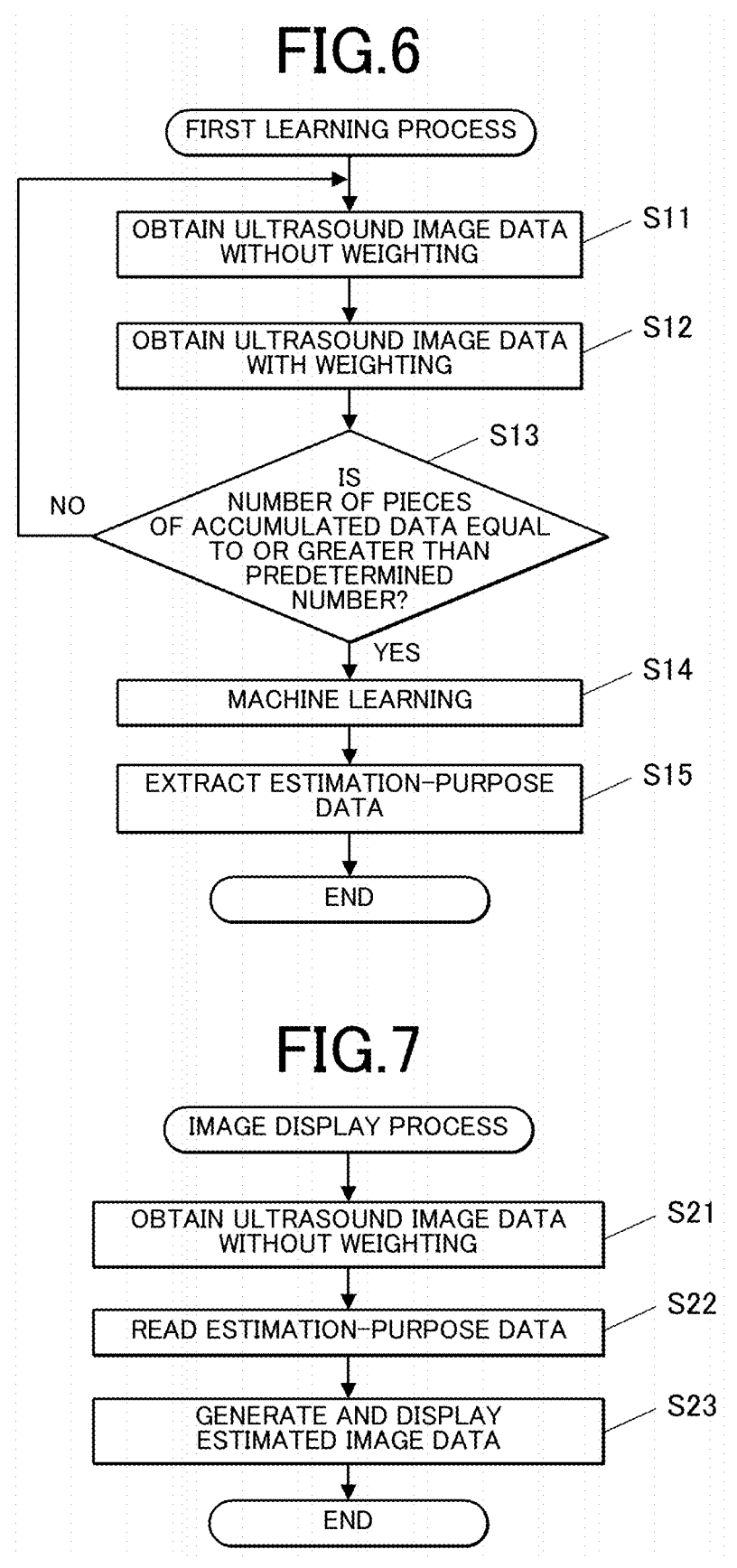

```
          ┌─────────────────────────────┐
          │    FIRST LEARNING PROCESS   │
          └─────────────────────────────┘
                        │
   ┌───────────────────▼──────────────────┐
   │ │  OBTAIN ULTRASOUND IMAGE DATA │──── S11
   │ │       WITHOUT WEIGHTING       │
   │ └──────────────┬────────────────┘
   │                ▼
   │ ┌──────────────────────────────┐
   │ │  OBTAIN ULTRASOUND IMAGE DATA │──── S12
   │ │        WITH WEIGHTING         │
   │ └──────────────┬────────────────┘
   │                ▼
   │                              S13
   │              ◇ IS
   │         NUMBER OF PIECES
   │  NO   OF ACCUMULATED DATA EQUAL
   │◀──────  TO OR GREATER THAN
   │          PREDETERMINED
   │             NUMBER? ◇
   │                │ YES
   │                ▼
     ┌──────────────────────────────┐
     │       MACHINE LEARNING        │──── S14
     └──────────────┬────────────────┘
                    ▼
     ┌──────────────────────────────┐
     │  EXTRACT ESTIMATION-PURPOSE   │──── S15
     │            DATA               │
     └──────────────┬────────────────┘
                    ▼
          ┌──────────────┐
          │     END      │
          └──────────────┘
```

FIG.7

```
          ┌─────────────────────────────┐
          │    IMAGE DISPLAY PROCESS    │
          └─────────────────────────────┘
                        │
                        ▼
     ┌──────────────────────────────┐
     │  OBTAIN ULTRASOUND IMAGE DATA │──── S21
     │       WITHOUT WEIGHTING       │
     └──────────────┬────────────────┘
                    ▼
     ┌──────────────────────────────┐
     │  READ ESTIMATION-PURPOSE DATA │──── S22
     └──────────────┬────────────────┘
                    ▼
     ┌──────────────────────────────┐
     │     GENERATE AND DISPLAY      │──── S23
     │     ESTIMATED IMAGE DATA      │
     └──────────────┬────────────────┘
                    ▼
          ┌──────────────┐
          │     END      │
          └──────────────┘
```

FIG.8

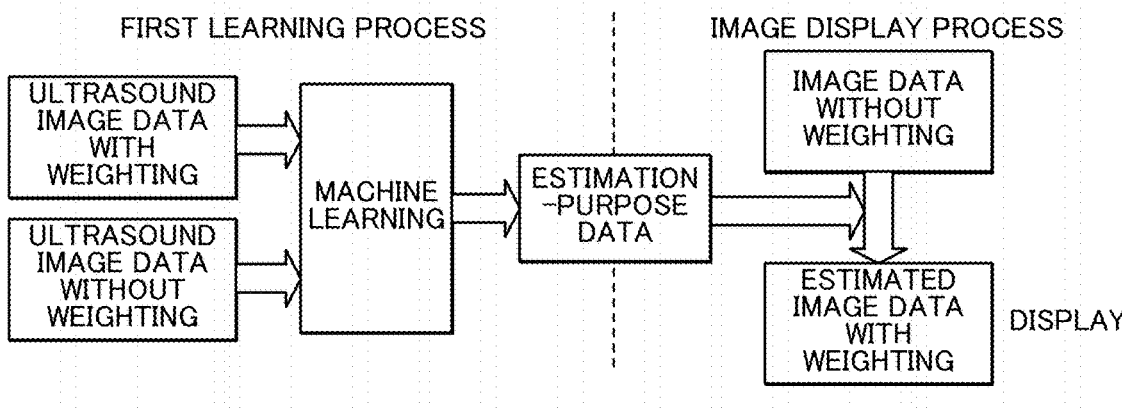

FIRST LEARNING PROCESS      IMAGE DISPLAY PROCESS

FIG.9

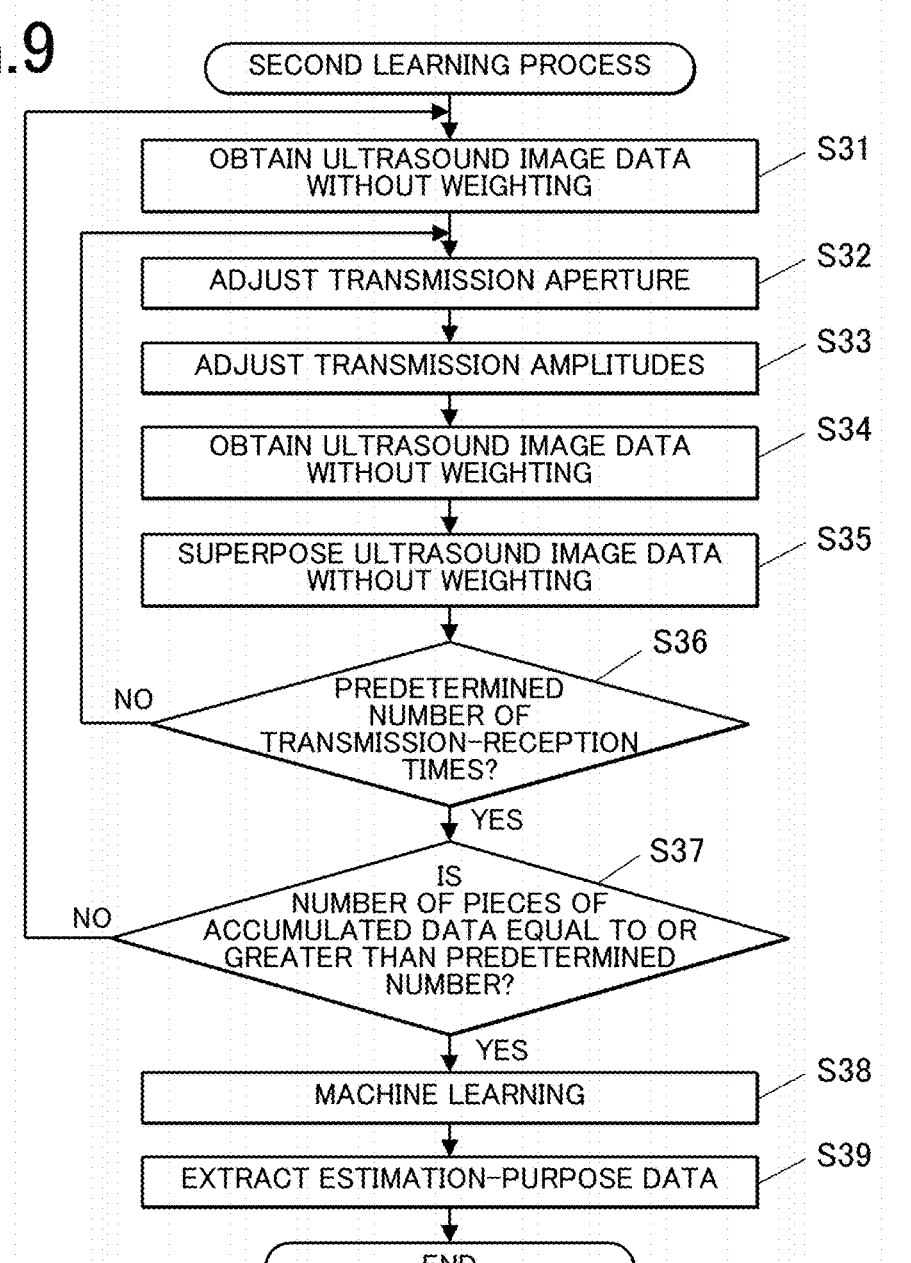

SECOND LEARNING PROCESS

OBTAIN ULTRASOUND IMAGE DATA WITHOUT WEIGHTING —— S31

ADJUST TRANSMISSION APERTURE —— S32

ADJUST TRANSMISSION AMPLITUDES —— S33

OBTAIN ULTRASOUND IMAGE DATA WITHOUT WEIGHTING —— S34

SUPERPOSE ULTRASOUND IMAGE DATA WITHOUT WEIGHTING —— S35

PREDETERMINED NUMBER OF TRANSMISSION-RECEPTION TIMES? —— S36    NO

YES

IS NUMBER OF PIECES OF ACCUMULATED DATA EQUAL TO OR GREATER THAN PREDETERMINED NUMBER? —— S37    NO

YES

MACHINE LEARNING —— S38

EXTRACT ESTIMATION-PURPOSE DATA —— S39

END

ULTRASOUND DIAGNOSTIC APPARATUS, ULTRASOUND DIAGNOSTIC SYSTEM, ULTRASOUND IMAGE GENERATION METHOD, AND STORAGE MEDIUM

CROSS-REFERENCE TO RELATED APPLICATIONS

The present invention claims priority under 35 U.S.C. § 119 to Japanese Patent Application No. 2023-200488 filed on Nov. 28, 2023, the entire contents of which being incorporated herein by reference.

TECHNICAL FIELD

The present invention relates to an ultrasound diagnostic apparatus, an information processing apparatus, an ultrasound diagnostic system, an ultrasound image generation method, an ultrasound image learning method, and a storage medium.

DESCRIPTION OF THE RELATED ART

There is known an ultrasound diagnostic apparatus configured to emit ultrasound waves from an ultrasound probe to the inside of a subject, receive reflected waves, and analyze the reflected waves to display an ultrasound image of the inside of the subject. The subject is a living body of a patient, for example.

The ultrasound probe includes transducers. Each of the transducers receives a transmission signal in the form of voltage pulses (transmission pulses) from the ultrasound diagnostic apparatus and emits an ultrasound wave. To change the voltage of transmission pulses applied to each transducer, a known ultrasound diagnostic apparatus includes multiple positive power supplies and negative power supplies having different voltages and switching elements for selectively switching the power supplies (see Japanese Patent No. 3665408). By switching the switching elements, the ultrasound diagnostic apparatus generates transmission pulses at a desired voltage and outputs the transmission pulses to the transducers.

There is also known a method to assign weights to transmission voltages for transmission pulses that are input to transducers of an ultrasound probe. Herein, with reference to FIG. 12 and FIG. 13, a configuration to assign weights to transmission pulses (drive voltage waveforms) that are input to transducers 211 of an ultrasound probe is described. FIG. 12 is a block diagram of transducers 211 and a transmitter 32 in a known art. FIG. 13 is a diagram showing the intensity of ultrasound waves corresponding to a position X in the scanning direction of the ultrasound probe 2.

An ultrasound diagnostic apparatus includes an ultrasound diagnostic apparatus main body, and an ultrasound probe connected to the main body. The ultrasound probe includes transducers 211. The transducers 211 include transducers 211a to 211l arranged in this order in the scanning direction. The ultrasound diagnostic apparatus main body includes a transmitter 32. The transmitter 32 includes a trigger circuit 321, a transmission power supply circuit 322, and pulsers 323. The pulsers 323 include pulsers 323a to 323l connected to the respective transducers 211a to 211l in this order.

Under the control of the controller (not illustrated), the trigger circuit 321 generates trigger signals for generating transmission pulses and outputs the signals to the respective pulsers 323a to 323l. The trigger circuit 321 applies, to the trigger signals, delay times set for the respective pulsers 323a to 323l.

The transmission power supply circuit 322 is constituted of multiple independent power supplies corresponding to the respective pulsers 323a to 323l. The transmission power supply circuit 322 supplies mutually independent and variable power supply voltages to the respective pulsers 323a to 323l under the control of the controller. The pulsers 323a to 323l generate transmission pulses corresponding to the power supply voltages supplied by the transmission power supply circuit 322 and transmit the generated transmission pulses to the respective transducers 211a to 211l under the control of the controller. The amplitudes of the transmission pulses generated by the pulsers 323a to 323l vary depending on the magnitude of the power supply voltage.

Herein, the aperture of the ultrasound probe is defined as the width of the transducers 211a to 211h. As an example, to converge the transmission beam, the trigger circuit 321 causes the transmission pulses from the end part of the aperture to be output at earlier timing and the transmission pulses from the central part of the aperture to be output at delayed timing. To obtain two dimensional ultrasound image data, the ultrasound diagnostic apparatus needs to gradually shift the position of the transmission beam to generate driving signals of transmission pulses and obtain reception signals. For example, the ultrasound diagnostic apparatus generates an ultrasound beam using the transducers 211a to 211h corresponding to the aperture, and then shifts the aperture in the scanning direction to generate a transmission beam using the transducers 211b to 211i. Accordingly, the position of the aperture is shifted by one transducer pitch. The position of the transmission beam is also shifted by one transducer pitch. Note that the timing of generating trigger signals by the trigger circuit 321 is also appropriately adjusted depending on the positions of the transducers used.

As shown in FIG. 12, assigning weights to transmission pulses commonly refers to setting drive voltage waveforms of transmission pulses such that amplitudes at the ends of the aperture are small and amplitudes at the center of the aperture are greatest. FIG. 13 shows intensities [dB] of an ultrasound wave with weighting of transmission pulses and an ultrasound wave without weighting of transmission pulses with respect to positions X [mm] in the scanning direction of the ultrasound probe. That is, FIG. 13 shows the directivity of a transmission beam of ultrasound waves with weighted transmission pulses and the directivity of a transmission beam of ultrasound waves with not-weighted transmission pulses. The graphs with weighting and without weighting are normalized at their respective maximum intensities. For not-weighted transmission pulses, transmission pulses to be input to the respective transducers have an equal amplitude. Accordingly, ultrasound pulses generated by the respective transducers have an equal amplitude. Not-weighted transmission pulses result in greater side lobes than weighted transmission pulses, as indicated by "{" at both shoulders of the graphs in FIG. 13. Greater side lobes may cause artifacts.

When weights are not assigned to transmission pulses, an ultrasound wave may be emitted in a direction deviated from a desired direction of the transmission beam. This is called a side lobe. When a reflective object is present in the direction of a side lobe, the reflective object appears in the ultrasound image even if there is no reflecting object in the desired transmission direction. This is called an artifact. Artifacts are undesirable because they deteriorate image quality and cause misdiagnosis. By assigning weights to transmission pulses, the level of side lobes in ultrasound images can be reduced; occurrence of artifacts can be restrained; and images having a good quality can be obtained.

There is also known an ultrasound diagnostic apparatus configured to use machine learning to improve ultrasound image quality. For example, Japanese Unexamined Patent Publication No. 2021-115212 discloses an ultrasound diagnostic apparatus having a machine learning model trained by a learning dataset including image data obtained by transmission of ultrasound plane wave beams or ultrasound convergent beams. By using the model and based on image data generated by plane wave beams, the ultrasound diagnostic apparatus generates estimated image data equivalent to image data obtained by convergent beams.

However, according to the ultrasound diagnostic apparatus of FIG. 12, the power supply voltage for performing weighting of transmission pulses needs to be adjusted each time the aperture position is changed. Usually, the power source output includes a capacitor for stabilization. Therefore, the transmitter 32 of the ultrasound diagnostic apparatus in FIG. 12 has power loss caused by charging and discharging of the capacitor, which generates heat. Furthermore, the transmitter 32 requires an increased physical amount of circuitry for assigning weights, which increase manufacturing costs. Furthermore, the ultrasound diagnostic apparatus of JP 2021-115212A is not configured to assign weights to transmission pulses.

An object of the present invention is to obtain ultrasound images with good image quality and reduce the physical quantity and cost of an ultrasound diagnostic apparatus.

SUMMARY OF THE INVENTION

In order to solve the above-described problem, according to an aspect of the present invention, there is provided an ultrasound diagnostic apparatus including a first hardware processor configured to estimate and generate weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

According to another aspect of the present invention, there is provided an ultrasound image generation method including: estimating and generating weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

According to another aspect of the present invention, there is provided a non-transitory computer-readable storage medium storing a program that causes a computer to function as a first hardware processor that estimates and generates weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 6 is a flowchart of a first learning process.

FIG. 7 is a flowchart of an image display process.

FIG. 8 is a schematic diagram of the first learning process and the image display process.

FIG. 9 is a flowchart of a second learning process.

DETAILED DESCRIPTION

Hereinafter, first and second embodiments of the present invention will be described in order with reference to the accompanying drawings. However, the scope of the invention is not limited to the illustrated examples.

First Embodiment

Figures 1, 2:
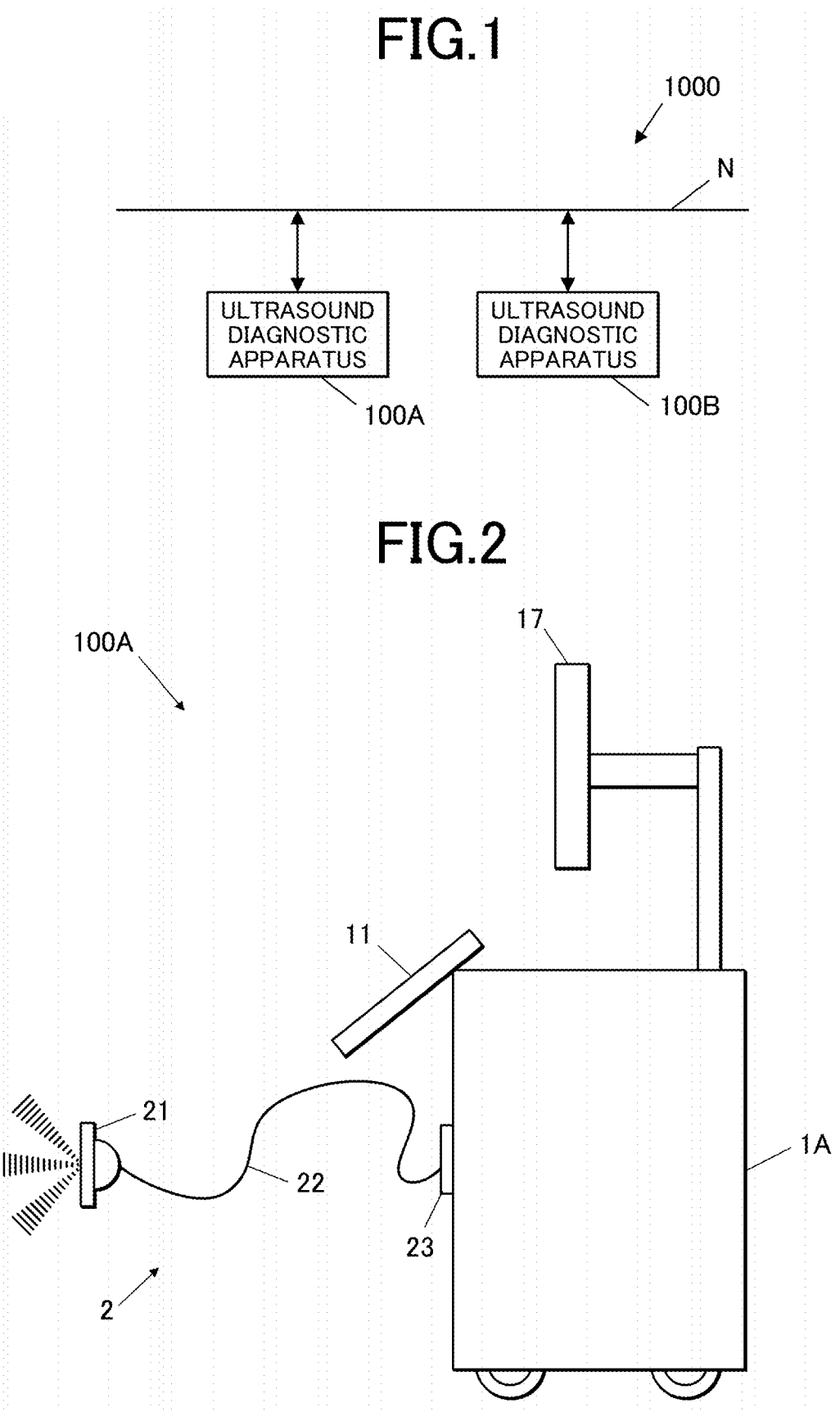
FIG. 1 is a block diagram of an ultrasound diagnostic system in a first embodiment of the present invention.
FIG. 2 is a schematic diagram of an ultrasound diagnostic apparatus configured to generate an estimated image using generated learning data.
Figure 3:
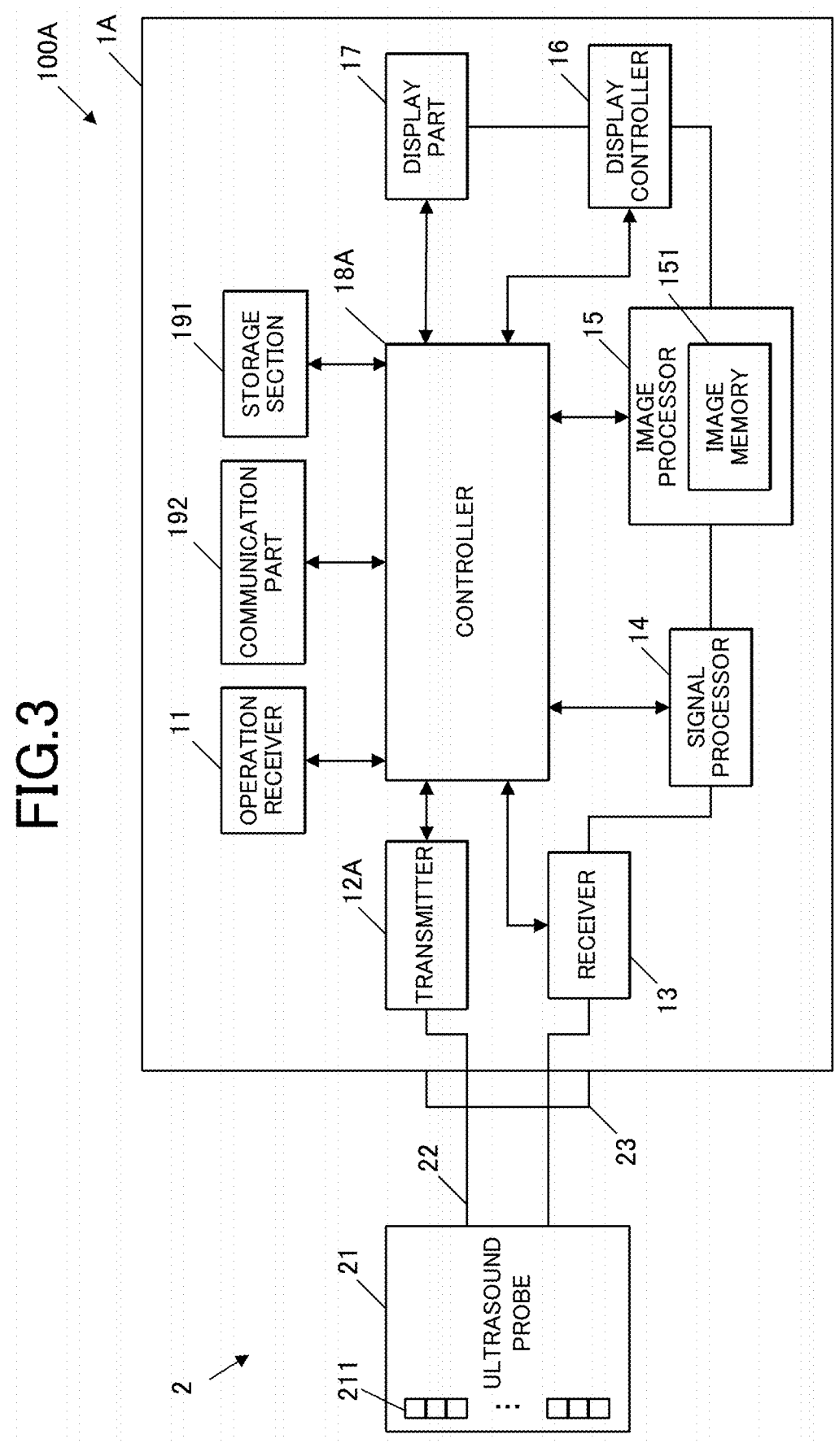
FIG. 3 is a block diagram showing a functional configuration of the ultrasound diagnostic apparatus configured to generate an estimated image using generated learning data.
Figure 4:
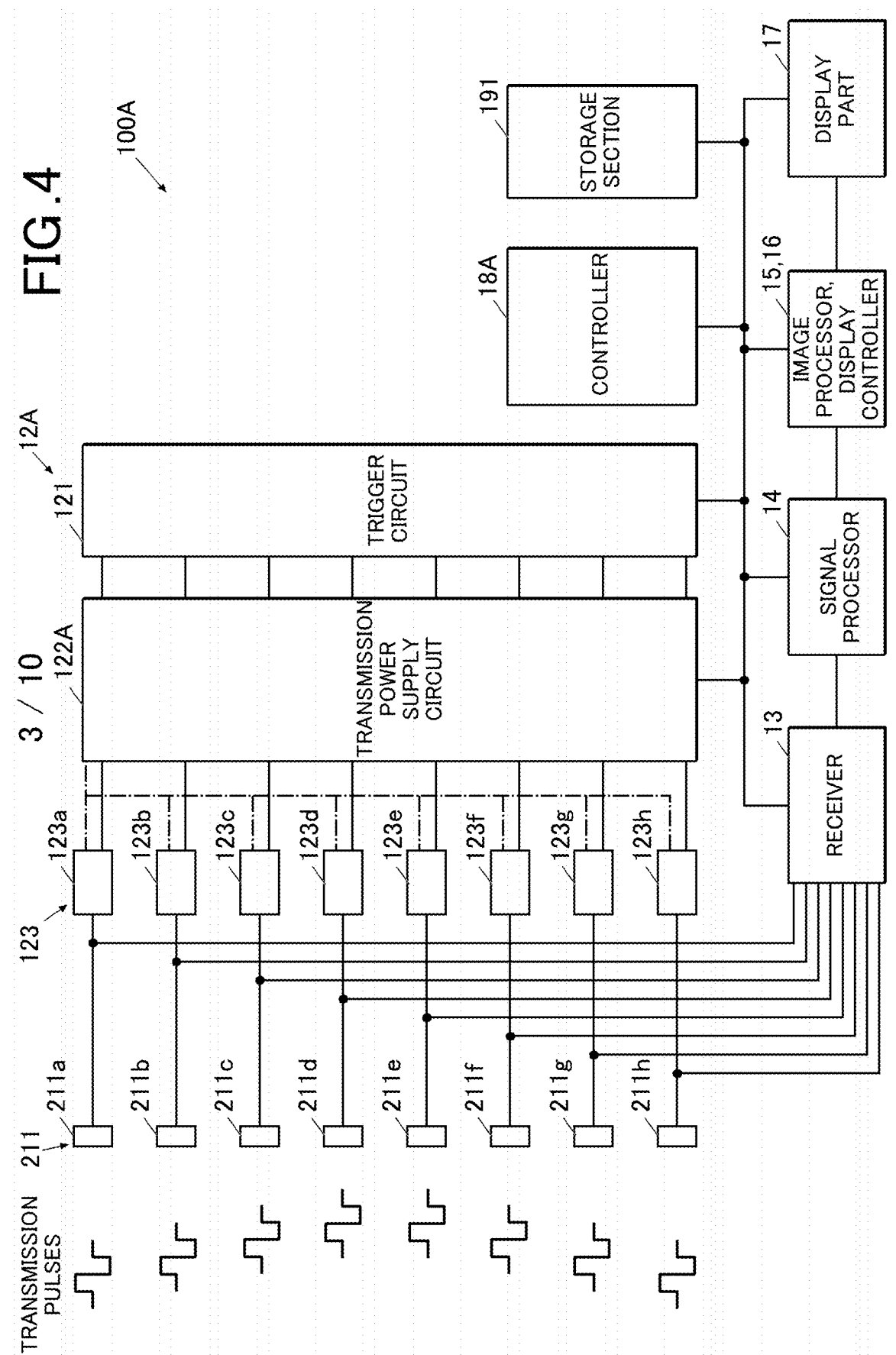
FIG. 4 is a block diagram of an internal configuration of a transmitter of the ultrasound diagnostic apparatus configured to generate an estimated image.
Figure 5:
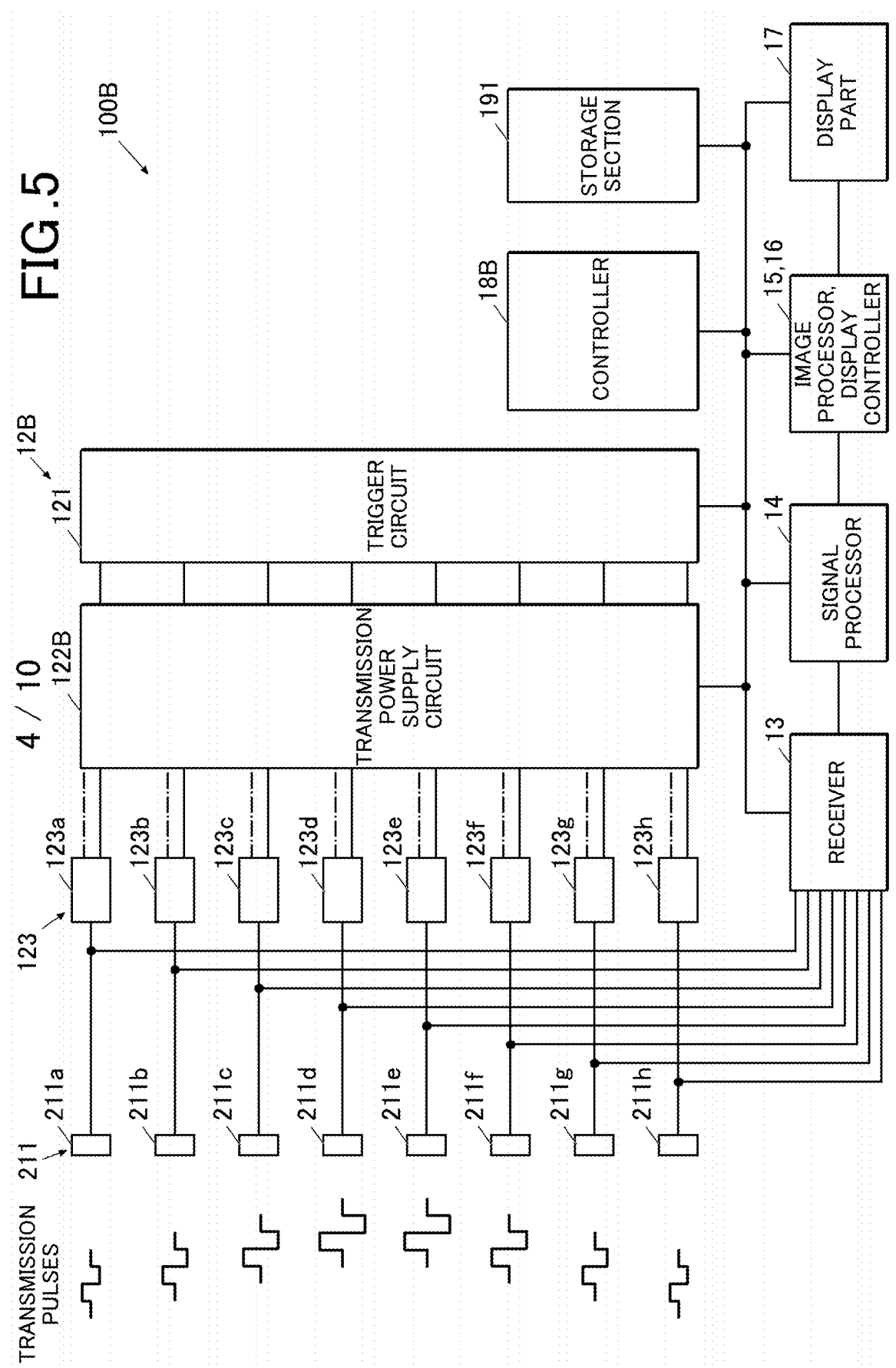
FIG. 5 is a block diagram of an internal configuration of a transmitter of an ultrasound diagnostic apparatus configured to generate learning data.

A first embodiment of the present invention will be described with reference to FIG. 1 to FIG. 8. First, the apparatus configuration of the present embodiment will be described with reference to FIG. 1 to FIG. 5. FIG. 1 is a block diagram of an ultrasound diagnostic system 1000 in a first embodiment of the present invention. FIG. 2 is a schematic diagram of an ultrasound diagnostic apparatus 100A that generates an estimated image using generated learning data. FIG. 3 is a block diagram showing a functional configuration of the ultrasound diagnostic apparatus 100A. FIG. 4 is a block diagram showing an internal configuration of a transmitter 12A of the ultrasound diagnostic apparatus 100A. FIG. 5 is a block diagram of an internal configuration of a transmitter 12B of an ultrasound diagnostic apparatus 100B configured to generate learning data according to the present embodiment.

As illustrated in FIG. 1, the ultrasound diagnostic system 1000 is a system provided in a medical facility, such as a medical apparatus developer or a hospital, and configured to estimate ultrasound image data using a learning model trained by machine learning. The ultrasound diagnostic system 1000 includes ultrasound diagnostic apparatuses 100A and 100B. The communication network N is, for example, a local area network (LAN) of a medical facility. At least the ultrasound diagnostic apparatuses 100A and 100B are connected to the communication network N.

The ultrasound diagnostic apparatuses 100A and 100B emit ultrasound waves to a subject such as a living body of a patient to generate ultrasound image data. The ultrasound diagnostic apparatus 100A is configured to generate an estimated image. The ultrasound diagnostic apparatus 100A generates and displays an estimated image using estimation-purpose data. The estimation-purpose data is a trained learning model obtained by the ultrasound diagnostic apparatus 100B.

The ultrasound diagnostic apparatus 100B is configured to perform learning. The ultrasound diagnostic apparatus 100B performs machine learning of ultrasound image data with and without weighting of transmission voltages to generate estimation-purpose data as a trained learning model.

As illustrated in FIG. 2, the ultrasound diagnostic apparatus 100A includes an ultrasound diagnostic apparatus main body 1A and an ultrasound probe 2. The ultrasound probe 2 is connected to the ultrasound diagnostic apparatus main body 1A. The ultrasound probe 2 transmits ultrasound waves (transmitted ultrasound waves) into a subject and receives ultrasound waves reflected inside the subject (reflected ultrasound waves: echoes). The ultrasound probe 2 has an ultrasound probe main body 21, a cable 22, and a connector 23. The ultrasound probe main body 21 is a header of the ultrasound probe 2 and transmits and receives ultrasound waves. The cable 22 is connected to the ultrasound probe main body 21 and the connector 23. Through the cable 22, driving signals for driving the ultrasound probe main body 21 and reception signals of ultrasound waves flow. The connector 23 is a plug to be connected to a receptacle connector (not illustrated) of the ultrasound diagnostic apparatus main body 1A.

The ultrasound diagnostic apparatus main body 1A is connected to the ultrasound probe main body 21 via the connector 23 and the cable 22. The ultrasound diagnostic apparatus main body 1A sends electric drive signals to the ultrasound probe main body 21, thereby causing the ultrasound probe main body 21 to transmit transmission ultrasound waves to the subject. Based on reflected ultrasound waves from the inside of the subject received by the ultrasound probe main body 21, the ultrasound probe 2 generates electric reception signals. Based on the reception signals generated by the ultrasound probe 2, the ultrasound diagnostic apparatus main body 1A images the internal state of the subject.

The ultrasound probe main body 21 has transducers 211 (FIG. 3) on the distal end side. The transducers 211 include transducers 211a to 211h (FIG. 4). The eight transducers 211a to 211h are the representatives of the transducers 211 for ease of description. The number of transducers 211 can be set as desired. The actual number of transducers is 192, for example.

Multiple transducers 211 are arranged, for example, in a one-dimensional array in a scanning direction (azimuth direction). The transducers 211 may be arranged in a two-dimensional array. In the present embodiment, the ultrasound probe 2 is a linear scanning type electronic scanning probe. However, the ultrasound probe 2 may be of either an electronic scanning type or a mechanical scanning type. In addition, the ultrasound probe 2 may be of any of a linear scanning type, a sector scanning type, and a convex scanning type. The ultrasound diagnostic apparatus main body 1A and the ultrasound probe 2 may communicate over wireless communication instead of wired communication via the cable 22. The wireless communication is an ultra-wide band (UWB), for example.

The operation receiver 11 is a control panel or the like configured to receive various operation inputs by a user, such as a doctor or a technician. The operation receiver 11 includes operational elements, such as a push button, an encoder, a lever switch, a joystick, a trackball, a keyboard, a touch pad, and/or a multifunction switch.

The display part 17 includes a display panel such as a liquid crystal display (LCD), an organic electro-luminescence (EL) display, or an inorganic EL display. The display part 17 displays display information such as ultrasound image data on the display panel.

As illustrated in FIG. 3, the ultrasound diagnostic apparatus main body 1A includes the operation receiver 11, the transmitter 12A, a receiver 13, a signal processor 14, an image processor 15, a display controller 16, the display part 17, a controller 18A, a storage section 191, and a communication part 192. The controller 18A functions as a first controller (first hardware processor).

The operation receiver 11 receives various operation inputs by the user and outputs operation signals to the controller 18A. The operation receiver 11 may include a touch screen formed integrally with the display screen of the display part 17 and configured to receive touch inputs by the user.

The transmitter 12A supplies electric drive signals to the ultrasound probe 2 under the control of the controller 18A and causes the ultrasound probe 2 to generate transmission ultrasound waves. Here, an internal configuration of the transmitter 12A will be described with reference to FIG. 4. The transmitter 12A includes a trigger circuit 121, a transmission power supply circuit 122A, and pulsers 123.

The pulsers 123 representatively include eight independent pulsers 123a to 123h for ease of explanation. However, the number of pulsers 123 is not limited to eight. The pulsers 123a to 123h are connected to the respective transducers 211a to 211h in this order.

The trigger circuit 121 includes a delay circuit. Under the control of the controller 18A, the trigger circuit 121 generates trigger signals for generating transmission pulses and outputs the trigger signals to the pulsers 123a to 123h. The trigger circuit 121 sets a delay time for each of the individual paths corresponding to the respective transducers 211. With the delay circuit, the trigger circuit 121 generates trigger signals that are delayed by the set delay times. By the trigger signals, the trigger circuit 121 delays transmission of transmission pulses corresponding to drive signals for driving the pulsers 123a to 123h. By the delaying, the trigger circuit 121 converges transmission beams consisting of the transmission ultrasound waves.

The transmission power supply circuit 122A is a single power supply corresponding to the pulsers 123a to 123h. Under the control of the controller 18A, the transmission power supply circuit 122A supplies a common and variable power supply voltage to the pulsers 123a to 123h. Under the control of the controller 18A, the pulsers 123a to 123h generate transmission pulses based on the power supply voltage supplied by the transmission power supply circuit 122A and transmit the transmission pulses to the respective transducers 211a to 211h. The transducers 211a to 211h are regarded as a transmission aperture. That is, the transmission pulses generated by the pulsers 123a to 123h are transmitted at different timings (with different amounts of delay), for example, as illustrated in FIG. 4. The transmission pulses generated by the pulsers 123a to 123h have the same amplitude. Therefore, the transmitter 12A cannot assign weights to the transmission voltages for the transmission pulses.

The transmitter 12A drives a successive part of the multiple transducers 211 arranged in the ultrasound probe 2 to generate transmission ultrasound waves. For example, the transmitter 12A drives successive 64 transducers 211 among 192 transducers 211. The transmitter 12A then performs scanning by changing the driven transducers 211 in the scanning direction each time transmission ultrasound waves are generated.

As shown in FIG. 3 and FIG. 4, the receiver 13 receives electric reception signals from the ultrasound probe 2 under the control of the controller 18A. The receiver 13 includes, for example, an amplifier, an A/D conversion circuit, and a phasing addition circuit. The amplifier amplifies the reception signals at amplification factors, which are set beforehand for the respective individual paths corresponding to the respective transducers 211. The A/D conversion circuit performs analog-to-digital conversion (A/D conversion) on the amplified reception signals. The phasing addition circuit applies, to the A/D converted reception signals, delay times determined for the respective individual paths corresponding to the respective transducers 211, thereby adjusting the time phase. After the above processes, the phasing addition circuit generates sound ray data by adding up the reception signals (phasing addition).

Under the control of the controller 18A, the signal processor 14 performs an envelope detection process, logarithmic compression, and so forth on the sound ray data generated by the receiver 13. After the above processes, the signal processor 14 further adjusts the dynamic range and the gain of the sound ray data to convert the data into brightness. By the brightness conversion, the signal processor 14 generates brightness mode (B-mode) image data constituted of pixels having brightness values corresponding to received energy. That is, the B-mode image data represents the intensity of the reception signals by brightness. The signal processor 14 may be configured to generate image data in an image mode other than the B mode, such as a motion (M) mode or a color Doppler mode.

The image processor 15 includes an image memory 15a. The image memory 15a is constituted of a semi-conductor memory, such as a dynamic random access memory (DRAM), for example. Under the control of the controller 18A, the image processor 15 stores the B-mode image data, which is sent from the signal processor 14, in the image memory 15a in units of frames. The B-mode image data in units of frames may be referred to as ultrasound image data.

Under the control of the controller 18A, the image processor 15 sends the ultrasound image data stored in the image memory 15a to the display controller 16 frame by frame at predetermined time intervals.

The display controller 16 is, for example, a digital scan converter (DSC). Under the control of the controller 18A, the display controller 16 performs processing such as coordinate conversion on the B-mode image data, which is input by the image processor 15, to convert the data into image signals for display. The display controller 16 outputs the image signals to the display part 17.

Under the control of the controller 18A, the display part 17 displays an ultrasound image on the display panel, based on the image signals output by the display controller 16. The display part 17 also displays various kinds of display information input by the controller 18A on the display panel.

The controller 18A includes, for example, a central processing unit (CPU), a read only memory (ROM), and a random access memory (RAM). The controller 18A reads various processing programs stored in the ROM, loads them in the RAM, and controls the components of the ultrasound diagnostic apparatus 100A in cooperation with the loaded programs and the CPU.

The ROM includes a nonvolatile memory such as a semiconductor. The ROM stores a system program corresponding to the ultrasound diagnostic apparatus 100A, various processing programs executable on the system program, and various kinds of information such as a gamma table. In particular, the ROM stores an image display program for executing an image display process, which is described later. These programs are stored in the RAM in the form of computer-readable program codes. The CPU sequentially executes operations according to the program codes on the RAM. The RAM forms a work area in which various programs executed by the CPU and data related to these programs are temporarily stored.

The storage section 191 is a hard disk drive (HDD), a solid state drive (SSD), or the like that stores information such as ultrasound image data in a writable and readable manner. The storage section 191 stores estimation-purpose data as a trained learning model, which is for estimating weighted ultrasound image data with weighing of transmission voltages from not-weighted ultrasound image data without weighting of transmission voltages.

The communication part 192 is a communication interface such as a network card connected to the communication network N. The controller 18A sends and receives information to and from an apparatus(es), such as the ultrasound diagnostic apparatus 100B, over the communication network N via the communication part 192.

Next, a configuration of the ultrasound diagnostic apparatus 100B for learning will be described with reference to FIG. 5. The ultrasound diagnostic apparatus 100B has a configuration in which the transmitter 12A and the controller 18A of the ultrasound diagnostic apparatus 100A are replaced with a transmitter 12B and a controller 18B, respectively. The controller 18B functions as a second controller (second hardware processor). The transmitter 12B includes a trigger circuit 121, a transmission power supply circuit 122B, and pulsers 123. The components of the ultrasound diagnostic apparatus 100B common to the components of the ultrasound diagnostic apparatus 100A are denoted by the same reference signs, and description thereof is omitted.

The transmission power supply circuit 122B is configured to supply independent and different power supply voltages to the respective pulsers 123a to 123h. That is, the transmission power supply circuit 122B can output, to the pulsers 123*a* to 123*h*, both (i) power supply voltages that assign weights to the transmission voltages and (ii) power supply voltages that do not assign weights to the transmission voltages. Therefore, the pulsers 123 can generate both (i) transmission pulses corresponding to voltages assigned with weights for transmission beams and (ii) transmission pulses corresponding to voltages not assigned with weights for transmission beams. That is, for example, as illustrated in FIG. 5, the weighted transmission pulses generated by the pulsers 123*a* to 123*h* of the transmitter 12B have different amplitudes and are transmitted at different timings (with different amounts of delay). Thus, the transmitter 12B can assign weights to voltages for transmitting the transmission pulses.

Furthermore, the transmission power supply circuit 122B and the pulsers 123 can switch between assigning weights and not assigning weights in a short period. For example, it is possible to switch between assigning weights and not assigning weights for each frame or for each time of transmission. Therefore, the ultrasound diagnostic apparatus 100B can obtain an ultrasound image data by switching between weighting and non-weighting in imaging a moving subject, such as a human body.

The controller 18B has the same configuration as the controller 18A. However, instead of the image display program, the ROM of the controller 18B stores a first learning program for executing a first learning process to be described later.

Next, with reference to FIG. 6 to FIG. 8, operations of the ultrasound diagnostic apparatuses 100A and 100B according to the present embodiment will be described. FIG. 6 is a flowchart illustrating the first learning process. FIG. 7 is a flowchart illustrating the image display process. FIG. 8 is a schematic diagram of the first learning process and the image display process.

First, the first learning process by the ultrasound diagnostic apparatus 100B will be described with reference to FIG. 6. In the first learning process, ultrasound image data of a subject, such as a patient serving as a learning sample, is obtained by assigning and not assigning weights to transmission voltages as training data, and machine learning is performed.

At the ultrasound diagnostic apparatus 100B, for example, an instruction to perform the first learning process is input by the user via the operation receiver 11. In response to the instruction to perform the first learning process, the controller 18B executes the first learning process in accordance with the first learning program stored in the ROM.

First, by controlling the transmitter 12B to the display controller 16, the controller 18B obtains not-weighted ultrasound image data without assigning weights to transmission voltages and stores the obtained data in the storage section 191 (step S11). By controlling the transmitter 12B to the display controller 16, the controller 18B obtains weighted ultrasound image data by assigning weights to transmission voltages and stores the obtained data in the storage section 191 (step S12).

The controller 18B determines whether the number of accumulated pieces of weighted and not-weighted ultrasound image data stored in the storage section 191 is equal to or greater than a predetermined number (step S13). The predetermined number in step S13 is the number sufficient for machine learning of weighted and not-weighted ultrasound image data. In machine learning, for example, the weighted and not-weighted ultrasound image data accumulated in the storage section 191 is used as training data to estimate the boundaries of feature quantities between weighted ultrasound image data and not-weighted ultrasound image data. Further, in machine learning, the boundaries of feature quantities are used to generate estimation-purpose data for estimating weighted ultrasound image data from not-weighted ultrasound image data.

When the number is less than the predetermined number (step S13; NO), the process proceeds to step S11. When the number is equal to or greater than the predetermined number (step S13; YES), the controller 18B performs machine learning using the weighted ultrasound image data and the not-weighted ultrasound image data stored in the storage section 191 (step S14). The controller 18B extracts estimation-purpose data from the machine learning result in step S14 and stores the result in the storage section 191 (step S15). Then the first learning process ends. As illustrated on the left side of the dotted line in FIG. 8, the estimation-purpose data is obtained by machine learning of weighted and not-weighted ultrasound image data of a sample subject.

The controller 18B sends the estimation-purpose data stored in the storage section 191 to the ultrasound diagnostic apparatus 100A, which is configured to generate an estimated image, via the communication part 192, for example. The controller 18A receives the estimation-purpose data from the ultrasound diagnostic apparatus 100B via the communication part 192 and stores the data in the storage section 191 of the ultrasound diagnostic apparatus 100A. Sending the estimation-purpose data from the ultrasound diagnostic apparatus 100B to the ultrasound diagnostic apparatus 100A may not be performed over the communication network N. For example, the ultrasound diagnostic apparatuses 100A and 100B may have a connector for recording media, such as a universal serial bus (USB) memory. The user connects a recording medium to the ultrasound diagnostic apparatus 100B and stores the generated estimation-purpose data in the recording medium. The user then connects the recording medium to the ultrasound diagnostic apparatus 100A and stores the estimation-purpose data in the storage section 191. Furthermore, the estimation-purpose data generated beforehand may be incorporated in a part of the system of the ultrasound diagnostic apparatus 100A. For example, the estimation-purpose data may be included in the image display program.

Next, the image display process by the ultrasound diagnostic apparatus 100A will be described with reference to FIG. 7. The image display process is to obtain ultrasound image data of a subject, such as a diagnosis-target patient, without assigning weights to transmission voltages and to estimate, generate, and display estimated image data.

After the first learning process, at the ultrasound diagnostic apparatus 100A, the user inputs an instruction to execute the image display process via the operation receiver 11, for example. In response to the instruction, the controller 18A executes the image display process in accordance with the image display program stored in the ROM.

First, by controlling the transmitter 12A to the display controller 16, the controller 18A acquires not-weighted ultrasound image data of a diagnosis-target subject without assigning weights to transmission voltages (step S21). The controller 18A reads the estimation-purpose data from the storage section 191 (step S22). By using the read estimation-purpose data, the controller 18A estimates and generates weighted ultrasound image data from the not-weighted ultrasound image data obtained in step S21 (step S23). The estimated and generated weighted ultrasound image data is referred to as estimated image data. In step S23, the controller 18A causes the display part 17 to display the estimated image data, which is generated weighted ultrasound image data. Then the image display process ends. As shown on the right side of the dotted line in FIG. 8, the estimated weighted image data of the diagnosis-target subject is obtained and displayed, based on the estimation-purpose data and the not-weighted ultrasound image data of the diagnosis-target subject.

It is preferable that image generation conditions of weighted and not-weighted ultrasound image data in the first learning process correspond to image generation conditions of not-weighted ultrasound image data in the image display process. The image generation conditions include transmission conditions other than the presence/absence of weighting of transmission voltages, reception conditions, and various processing conditions related to generation of ultrasound image data, such as an image mode and image processing. The image generation conditions may include the type and part of the subject.

As described above, according to the present embodiment, the ultrasound diagnostic system includes the ultrasound diagnostic apparatuses 100A and 100B. The ultrasound diagnostic apparatus 100A includes the controller 18A. The controller 18A estimates and generates image data with weighting of transmission voltages from image data without weighting of transmission voltages of the ultrasound waves emitted by the transducers 211 of the ultrasound probe 2, by using the estimation-purpose data. The estimation-purpose data is obtained by machine learning of image data with weighting and image data without weighting as training data. The estimation-purpose data is for estimating image data with weighting from image data without weighting.

According to such a configuration, the ultrasound diagnostic apparatus 100A can obtain an ultrasound image having excellent image quality from the estimated image data with weighting. Furthermore, the ultrasound diagnostic apparatus 100A does not require the transmission power supply circuit 122B configured to assign weights but includes the transmission power supply circuit 122A not configured to assign weights. Therefore, the physical quantity, cost, and heat generation of the ultrasound diagnostic apparatus 100A can be reduced.

The ultrasound diagnostic apparatus 100B includes the controller 18B. The controller 18B performs machine learning by using training data that includes (i) weighted image data obtained by assigning weights to ultrasound waves emitted by multiple transducers 211 and (ii) not-weighted image data obtained without assigning weights to ultrasound waves emitted by multiple transducers 211. By the machine learning, the controller 18B generates estimation-purpose data for estimating weighted image data from not-weighted image data.

Therefore, the ultrasound diagnostic apparatus 100B allows the ultrasound diagnostic apparatus 100A to estimate weighted image data based on the estimation-purpose data and to obtain a high-quality ultrasound image from the estimated image data.

Second Embodiment

Figure 10:
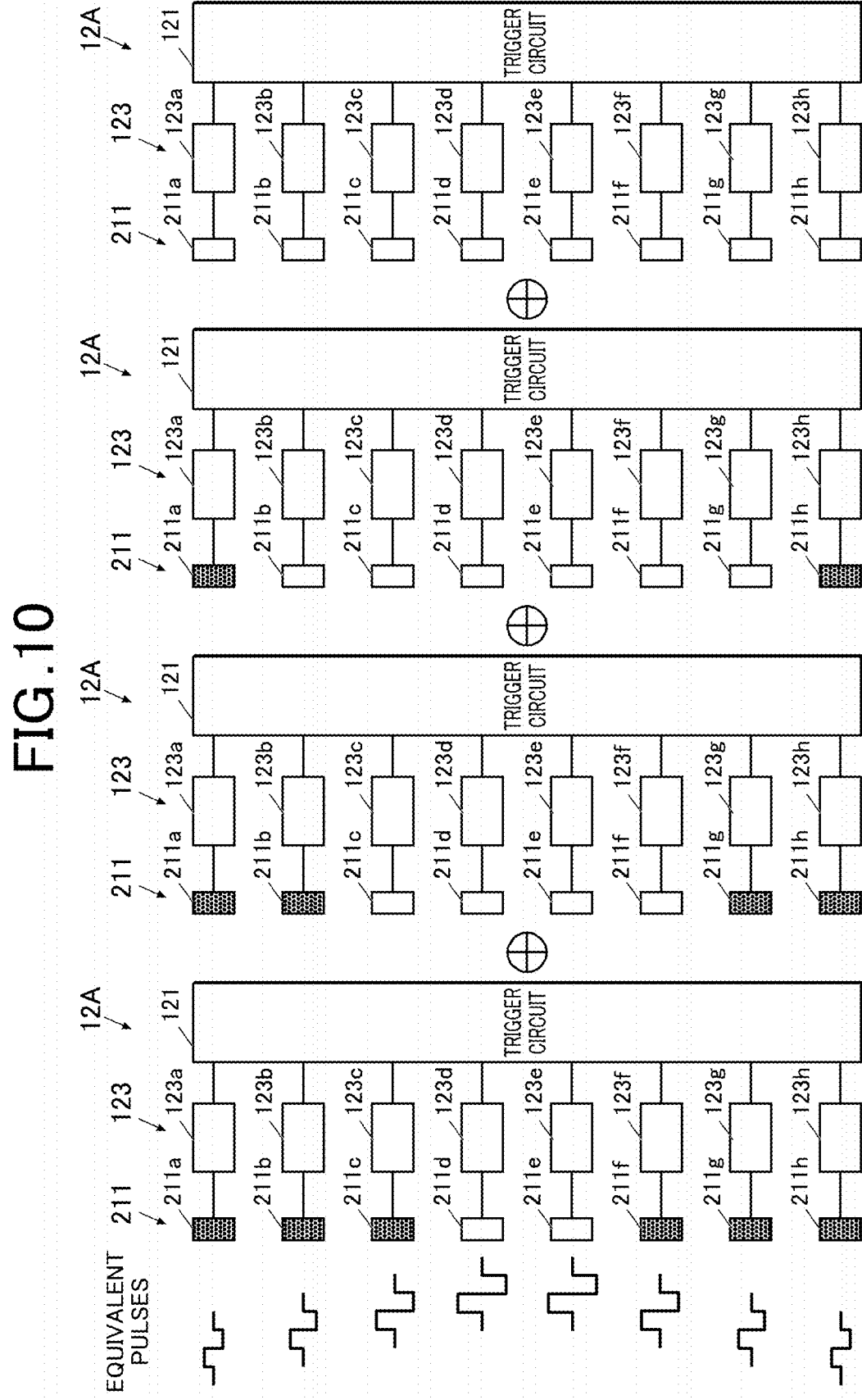
FIG. 10 is a diagram showing first to fourth transmissions and receptions by a transmitter and superposing of ultrasound image data in a second embodiment.
Figure 11:
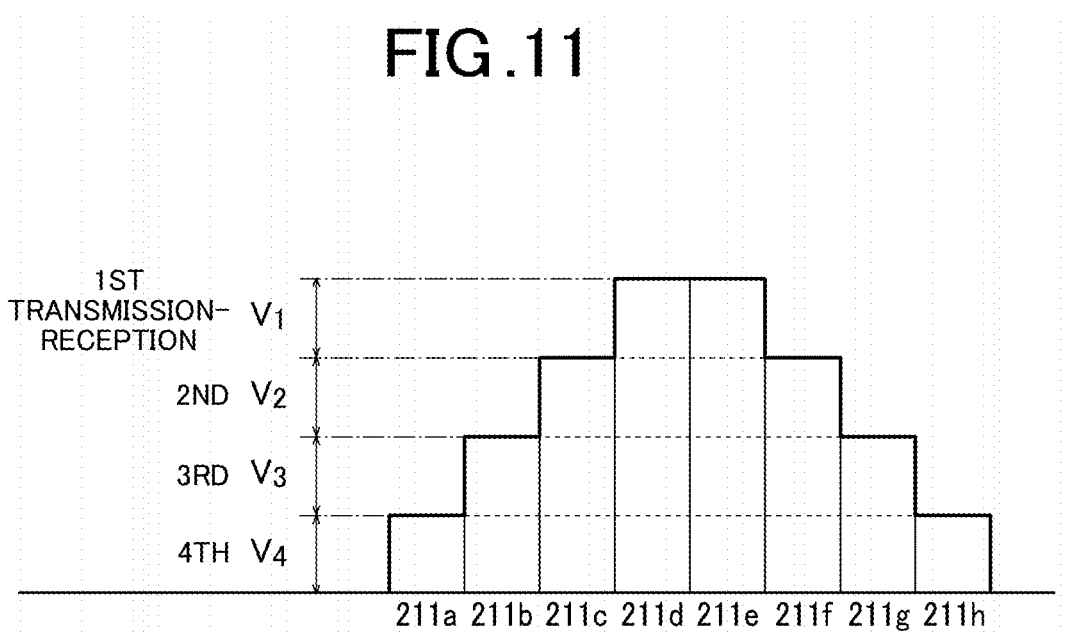
FIG. 11 is a diagram showing voltages of weighted equivalent pulses at first to fourth transmissions and receptions by the transmitter of FIG. 10.
Figure 12:
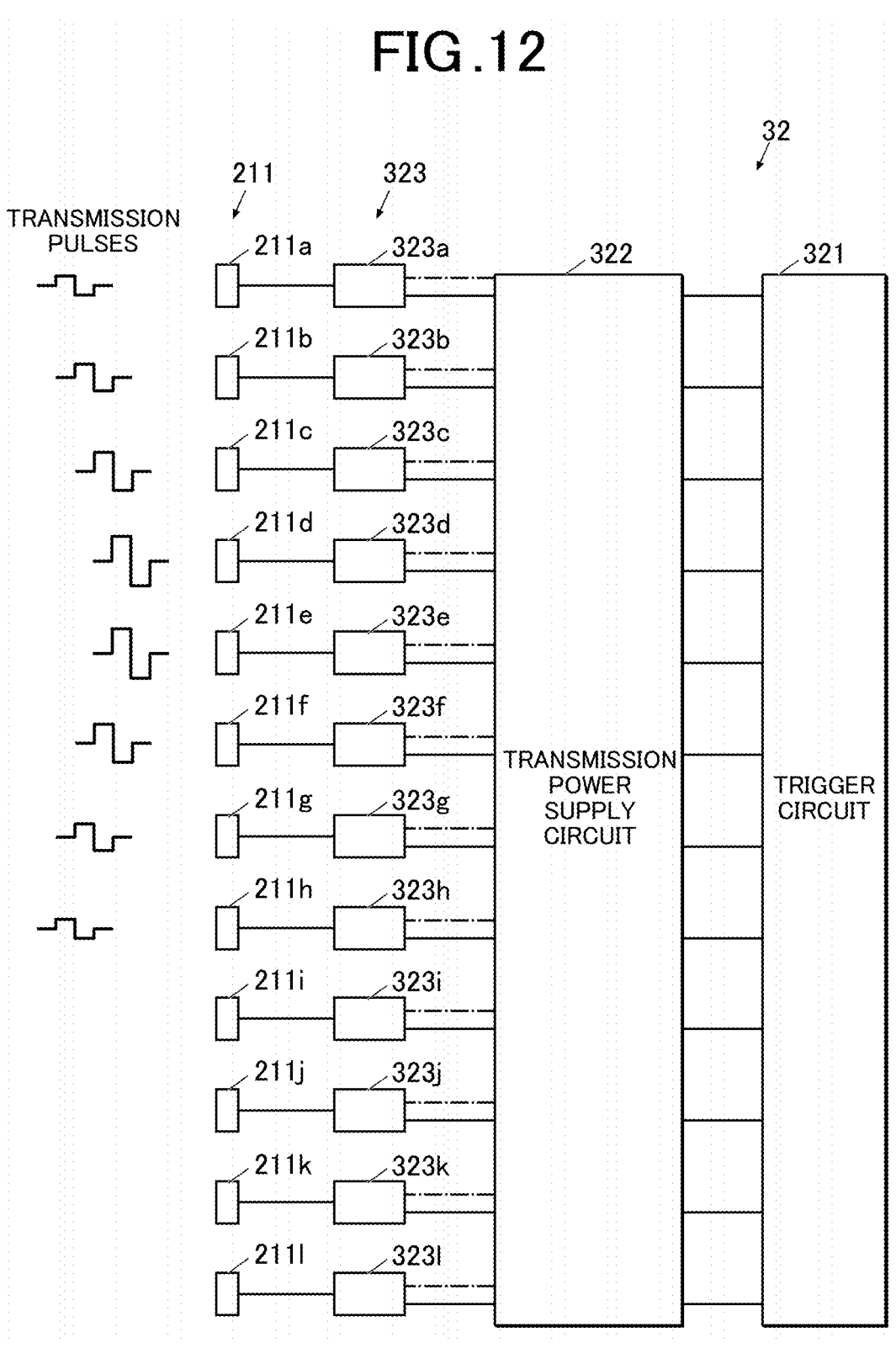
FIG. 12 is a block diagram showing transducers and a transmitter in the known art.
Figure 13:
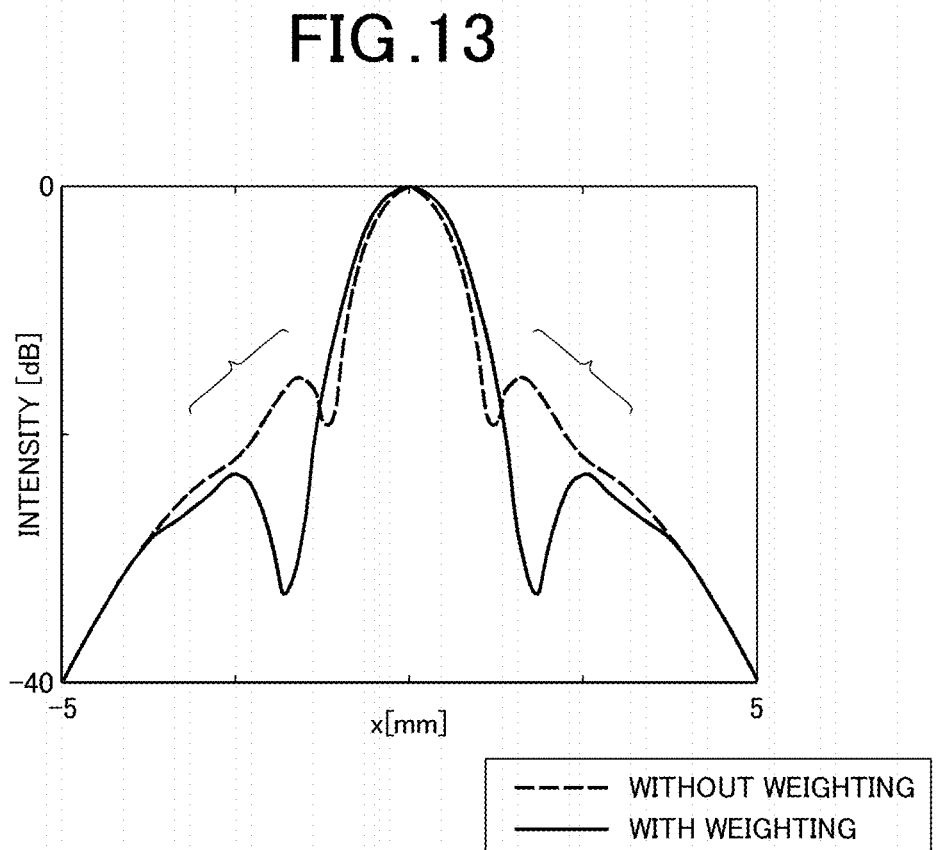
FIG. 13 is a diagram showing the intensity of ultrasound waves with respect to positions in the scanning direction of the ultrasound probe.

A second embodiment of the present invention will be described with reference to FIG. 9 to FIG. 11. FIG. 9 is a flowchart of a second learning process. FIG. 10 is a diagram showing first to fourth transmissions by the transmitter 12A and superposing of ultrasound image data in the second embodiment. FIG. 11 is a diagram showing voltages of weighted equivalent pulses in first to fourth transmissions and receptions by the transmitter 12A of FIG. 10.

In the first embodiment, the ultrasound diagnostic apparatus 100B is configured to perform machine learning based on weighted ultrasound data, which is obtained by assigning weights to transmission pulses, and not-weighted ultrasound data, which is obtained without assigning weights to transmission voltages. In the second embodiment, the ultrasound diagnostic apparatus 100A is configured to generate ultrasound data equivalent to weighted ultrasound data by superposing not-weighted ultrasound data and perform machine learning.

In the present embodiment, the ultrasound diagnostic apparatus 100A is used. The ROM of the controller 18A stores the image display program and a second learning program for executing a second learning process, which is described later. Note that the ultrasound diagnostic apparatus 100B may be used.

With reference to FIG. 9 to FIG. 11, operations of the ultrasound diagnostic apparatus 100A according to the present embodiment will be described. The second learning process by the ultrasound diagnostic apparatus 100A will be described with reference to FIG. 9. The second learning process is to obtain, as training data, weighted and not-weighted ultrasound image data of a subject, such as a patient serving as a learning sample, with and without weighting of transmission voltages and to perform machine learning. The weighted ultrasound image data is obtained by superposing multiple pieces of not-weighted ultrasound image data.

At the ultrasound diagnostic apparatus 100A, for example, the user inputs an instruction to perform the second learning process via the operation receiver 11. In response to the instruction, the controller 18A executes the second learning process in accordance with the second learning program stored in the ROM.

First, by controlling the transmitter 12A to the display controller 16, the controller 18A acquires not-weighted ultrasound image data without assigning weights to transmission voltages and stores the data in the storage section 191 (step S31). The controller 18A adjusts and sets the transmission aperture and the delay amounts corresponding to the current number of transmission-reception times to the trigger circuit 121, the transmission power supply circuit 122A, and the pulsers 123 (step S32). That is, in step S32, convergence conditions (the transmission aperture and the delay amounts) are set as transmission parameters. The controller 18A adjusts and sets the amplitudes of transmission pulses corresponding to the current number of transmission-reception times to the transmission power supply circuit 122A (step S33). That is, in step S33, transmission voltages are set as transmission parameters.

Herein, regarding steps S32 and S33, an example of transmitting transmission pulses when the predetermined number of transmission-reception times is four will be described with reference to FIG. 10. The predetermined number of transmission-reception times is a maximum number of transmission-reception times of ultrasound waves to obtain pieces of not-weighted ultrasound image data, which are to be superposed to generate superposed image data equivalent to a piece of weighted ultrasound image data.

Corresponding to step S32, the state of the transmitter 12A at each transmission-reception time will be described. The transmitter 12A at the first transmission-reception time turns on only the pulsers 123d and 123e of the transmission aperture among the pulsers 123 and transmits transmission pulses to only the transducers 211d and 211e. The transmitter 12A at the second transmission-reception time turns on only the pulsers 123c to 123f of the transmission aperture among the pulsers 123 and transmits transmission pulses to only the transducers 211c to 211f. The transmitter 12A at the third transmission-reception time turns on only the pulsers 123b to 123g of the transmission aperture among the pulsers 123 and transmits transmission pulses to only the transducers 211b to 211g. The transmitter 12A at the fourth transmission-reception time turns on the pulsers 123a to 123h of the transmission aperture among the pulsers 123 and transmits transmission pulses to the transducers 211a to 211h.

In step S33, the transmission pulses at the first to fourth transmission-reception times have the equal amplitude. Pieces of ultrasound image data obtained by the first to fourth transmission-reception times of ultrasound waves are superposed, and the superposed data is equivalent to the transmission of equivalent pulses shown in FIG. 10. The equivalent pulses have smaller amplitudes at the end sides of the transmission aperture of the transducers 211 in the scanning direction. The equivalent pulses have larger amplitudes in the central part of the transmission aperture.

As illustrated in FIG. 11, the amplitudes of the transmission pulses at the first to fourth transmission-reception times are referred to as voltages V1, V2, V3, and V4, respectively. Here, the voltages V1, V2, V3 and V4 are equal. The horizontal axis of the graph in FIG. 11 indicates the transducers 211a to 211h. The vertical axis indicates the voltages of the equivalent pulses. The voltages of the equivalent pulses corresponding to the transducers 211 at the first to fourth transmission-reception times are 4V1 and highest at the transducer 211d and 211e, and the voltages of the equivalent pulses are V1 and lowest at the transducers 211a and 211h. In step S33, the voltages of the amplitudes of the transmission pulses at each transmission-reception time may be changed to change the weighting curve.

Returning to FIG. 9, the controller 18A controls the transmitter 12B to the display controller 16, based on the transmission aperture and the amplitudes of the transmission pulses adjusted in steps S32 and S33 (step S34). By the control in step S34, the controller 18A obtains ultrasound image data without assigning weights to transmission voltages.

The controller 18A superposes the not-weighted ultrasound image data acquired in step S34 on not-weighted ultrasound image data stored in the storage section 191 (step S35). In step S35, the controller 18A stores the superposed ultrasound image data in the storage section 191 as weighted ultrasound image data.

The controller 18A determines whether the current number of transmission-reception times is the predetermined number of transmission-reception times (step S36). When the number of transmission-reception times is less than the predetermined number of transmission-reception times (step S36; NO), the process proceeds to step S32. When the number of transmission-reception times is less than the predetermined number of transmission-reception times (step S36: YES), the controller 18A determines whether or not the number of pieces of accumulated weighted and not-weighted ultrasound image data stored in the storage section 191 is equal to or greater than a predetermined number (step S37).

When the number is less than the predetermined number (step S37; NO), the process proceeds to step S31. When the number is equal to or greater than the predetermined number (step S37; YES), the controller 18A executes steps S38 and S39 and ends the second learning process. Steps S38 and S39 are the same as steps S14 and S15 of the first learning process in FIG. 6. After the second learning process, the ultrasound diagnostic apparatus 100A performs the image display process.

As described above, according to the second embodiment, the controller 18A of the ultrasound diagnostic apparatus 100A generates weighted image data with weighting of transmission voltages for machine learning. The weighted image data is generated by combining (superposing) multiple pieces of image data obtained by changing transmission parameters without weighting. The transmission parameters are transmission voltages and convergence conditions (the transmission aperture and the delay amounts). Therefore, in machine learning, multiple pieces of weighted image data for learning can be generated without a special apparatus (the transmission power supply circuit 122B).

In this method, it is not preferable to change the positional relationship between the transducers and the subject between multiple transmission-reception times in order to generate accurate weighting signals. Therefore, for example, an ultrasound phantom is used as the subject.

In the above description, although the ROMs of the controllers 18A, 18B are used as an example of the computer-readable media storing the programs according to the present invention, the present invention is not limited to this example. As other computer-readable media, a nonvolatile memory, such as a flash memory, and a portable recording medium, such as a CD-ROM, can be applied. Furthermore, a carrier wave is also applied as a medium for providing data of a program according to the present invention via a communication line.

The description in the above embodiment is an example of the ultrasound diagnostic apparatus, the information processing apparatus, the ultrasound diagnostic system, the ultrasound image generation method, the ultrasound image learning method, and the program according to the present invention. However, the present invention is not limited to the above embodiments.

In each of the above-described embodiments, estimation-purpose data is generated by performing machine learning of ultrasound image data as imaging-purpose data. Furthermore, each of the above-described embodiments is configured to generate estimated weighted image data from not-weighted ultrasound image data (imaging-purpose data) obtained without assigning weights to transmission voltages. However, the present invention is not limited to this configuration. The imaging-purpose data to be used for machine learning and estimation may be intermediate data that is generated between generation of sound ray data and generation of ultrasound image data. The intermediate data is, for example, sound ray data after envelope detection process is performed or sound ray data after logarithmic compression is performed.

In the first embodiment described above, the ultrasound diagnostic apparatus 100B as an information processing apparatus performs machine learning using weighted and not-weighted ultrasound image data with and without weighting of transmission voltages. However, the present invention is not limited to this configuration. For example, a server as an information processing apparatus may be provided on the communication network N. The server obtains weighted and not-weighted ultrasound image data generated by the ultrasound diagnostic apparatus 100B, performs machine learning using the obtained data, and generates estimation-purpose data. The server sends the estimation-purpose data to the ultrasound diagnostic apparatus 100A and stores the estimation-purpose data in the apparatus 100A.

Similarly, in the above-described second embodiment, a server may be provided on the communication network N to which the ultrasound diagnostic apparatus 100A is connected. The server obtains ultrasound image data with and without weighting generated by the ultrasound diagnostic apparatus 100A, performs machine learning using the obtained data, and generates estimation-purpose data. The server sends the estimation-purpose data to the ultrasound diagnostic apparatus 100A and stores the estimation-purpose data in the apparatus 100A.

Furthermore, the above-described second embodiment may be further included, on the communication network N, an ultrasound diagnostic apparatus 100A configured to generate an estimation-purpose image and an ultrasound diagnostic apparatus 100A configured to perform learning.

Furthermore, the detailed configurations and detailed operations of the ultrasound diagnostic system 1000 and the ultrasound diagnostic apparatuses 100A and 100B in the above-described embodiments can be appropriately changed without departing from the spirit of the present invention.

Although embodiments of the present invention have been described and shown in detail, the disclosed embodiments are made for purposes of illustration and example only and not limitation. The scope of the present invention should be interpreted by terms of the appended claims.

What is claimed is:

1. An ultrasound diagnostic apparatus comprising a first hardware processor configured to estimate and generate weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

2. The ultrasound diagnostic apparatus according to claim 1, wherein the weighted imaging-purpose training data for machine learning is generated by combining multiple pieces of not-weighted imaging-purpose data obtained by changing transmission parameters without assigning weights to transmission ultrasound waves.

3. The ultrasound diagnostic apparatus according to claim 2, wherein the transmission parameters include a transmission voltage and a convergence condition.

4. An ultrasound diagnostic system comprising:

the ultrasound diagnostic apparatus according to claim 1; and an information processing apparatus that includes a second hardware processor configured to generate the estimation-purpose data by performing machine learning of the weighted imaging-purpose training data obtained by assigning weights to transmission ultrasound waves emitted by transducers of an ultrasound probe and the not-weighted imaging-purpose training data obtained without assigning weights to transmission ultrasound waves.

5. An ultrasound image generation method comprising:

estimating and generating weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

6. A non-transitory computer-readable storage medium storing a program that causes a computer to function as a first hardware processor that estimates and generates weighted imaging-purpose data with weighting of transmission ultrasound waves emitted by transducers of an ultrasound probe from not-weighted imaging-purpose data obtained without assigning weights to transmission ultrasound waves by using estimation-purpose data for estimating weighted imaging-purpose data from not-weighted imaging-purpose data, the estimation-purpose data being obtained by machine learning of weighted imaging-purpose training data obtained by assigning weights to transmission ultrasound waves and not-weighted imaging-purpose training data obtained without assigning weights to transmission ultrasound waves.

* * * * *